United States Patent
Ron Edoute et al.

(10) Patent No.: US 9,532,832 B2
(45) Date of Patent: Jan. 3, 2017

(54) ESTHETIC DEVICE FOR BEAUTIFYING SKIN AND METHODS THEREOF

(75) Inventors: Oded Ron Edoute, Tel Aviv (IL); Orit Ron Edoute, Tel Aviv (IL); Vadim Polyakov, Petah Tikva (IL); Almog Zahavi, Tel-Aviv (IL)

(73) Assignee: VENUS CONCEPT LTD., Karmiel (IL)

(*) Notice: Subject to any disclaimer, the term of this patent is extended or adjusted under 35 U.S.C. 154(b) by 374 days.

(21) Appl. No.: 13/603,628

(22) Filed: Sep. 5, 2012

(65) Prior Publication Data
US 2013/0238062 A1 Sep. 12, 2013

Related U.S. Application Data

(60) Provisional application No. 61/531,025, filed on Sep. 5, 2011.

(51) Int. Cl.
| | | |
|---|---|---|
| *A61B 18/04* | (2006.01) | |
| *A61B 18/18* | (2006.01) | |
| *A61N 7/02* | (2006.01) | |
| *A61N 1/06* | (2006.01) | |
| *A61N 1/32* | (2006.01) | |
| *A61B 18/14* | (2006.01) | |

(Continued)

(52) U.S. Cl.
CPC ............ *A61B 18/18* (2013.01); *A61B 18/14* (2013.01); *A61N 1/06* (2013.01); *A61N 1/328* (2013.01); *A61N 7/02* (2013.01); *A61B 18/203* (2013.01); *A61B 2018/00005* (2013.01); *A61B 2018/0047* (2013.01); *A61B 2018/00452* (2013.01); *A61B 2018/00791* (2013.01); *A61B 2018/1467* (2013.01)

(58) Field of Classification Search
CPC .......... A61B 2018/00452; A61B 2018/00702; A61B 2018/00869
USPC ................................................... 606/32–35
See application file for complete search history.

(56) References Cited

U.S. PATENT DOCUMENTS

5,383,874 A * 1/1995 Jackson et al. .................. 606/1
5,620,481 A * 4/1997 Desai et al. .................. 607/101
(Continued)

FOREIGN PATENT DOCUMENTS

WO 98/05380 A1 2/1998

OTHER PUBLICATIONS

Venus Concept Ltd., "Esthetic Apparatus Useful for Increasing Skin Rejuvenation and Methods Thereof", co-pending U.S. Appl. No. 14/845,315, filed Sep. 4, 2015.

(Continued)

*Primary Examiner* — Ronald Hupczey
*Assistant Examiner* — Yasamin Ekrami

(57) ABSTRACT

A device for improving the cosmetic appearance of the skin is disclosed, wherein said device comprises RF generating means for generating N independent RF signals of predetermined waveforms, frequencies, amplitudes, and relative phases; control means for controlling the output of said RF generating means, said control means in communication with said RF generating means; N pairs of RF electrodes, each of said pairs in independent communication with said RF generating means, said RF electrodes configured to transmit RF energy to said skin; and an electrically insulating casing adapted to hold said RF electrodes such that said RF electrodes may be placed in simultaneous physical contact with said skin.

18 Claims, 4 Drawing Sheets

(51) Int. Cl.
    *A61B 18/20*        (2006.01)
    *A61B 18/00*        (2006.01)

(56) References Cited

U.S. PATENT DOCUMENTS

| | | |
|---|---|---|
| 6,277,116 B1* | 8/2001 | Utely et al. ............... 606/42 |
| 8,150,532 B2* | 4/2012 | Karni et al. ............... 607/101 |
| 2007/0053466 A1* | 3/2007 | Klostermann ............ 375/316 |
| 2007/0088413 A1* | 4/2007 | Weber ............ A61B 18/14 607/99 |
| 2008/0103545 A1* | 5/2008 | Bolea et al. ............... 607/42 |
| 2008/0234671 A1* | 9/2008 | Marion ..................... 606/41 |
| 2008/0281314 A1* | 11/2008 | Johnson et al. ........... 606/34 |
| 2009/0036958 A1* | 2/2009 | Mehta ...................... 607/99 |
| 2009/0248019 A1* | 10/2009 | Falkenstein et al. ...... 606/42 |
| 2010/0010480 A1* | 1/2010 | Mehta et al. ............. 606/9 |
| 2010/0016850 A1 | 1/2010 | Ron Edoute et al. |
| 2010/0030210 A1* | 2/2010 | Paulus ............ A61B 18/1206 606/38 |
| 2011/0009737 A1* | 1/2011 | Manstein .................. 600/424 |
| 2011/0202048 A1* | 8/2011 | Nebrigic ................... 606/22 |
| 2011/0202116 A1* | 8/2011 | Barolet et al. ............ 607/90 |
| 2013/0158634 A1 | 6/2013 | Ron Edoute et al. |
| 2013/0238061 A1 | 9/2013 | Ron Edoute et al. |

OTHER PUBLICATIONS

Venus Concept Ltd., "Device and Method for Fractional RF Treatment of the Skin", co-pending U.S. Appl. No. 14/989,826, filed Jan. 7, 2016.

\* cited by examiner

ESTHETIC DEVICE FOR BEAUTIFYING SKIN AND METHODS THEREOF

FIELD OF THE INVENTION

This invention generally relates to a device used to improve skin viability and skin rejuvenation via electrotherapy, and a method of using the device.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

The skin and muscles of the face are structured differently than other places on the body. One side of the facial muscles is connected to the bone and the other to the skin. As the muscle deteriorates through the aging process, the attached facial skin loses it elasticity. Loss of elasticity causes the skin to sag and wrinkle. Strengthening relevant muscle groups restores and maintains the original shape and contour of the muscles. As facial muscles get stronger, they get shorter and flatter, causing the attached skin to become firmer, and smoothing wrinkles, improving facial appearance. Additionally, a contracting muscle's blood supply is 10 times greater than a muscle at rest. This fresh blood supply delivers vital oxygen and nutrients to the skin, revitalizing the tissue.

The most common method of heating the dermis, is the use of RF radiation, applied by antenna or electrodes. For example, WO98005380 discloses a method of tightening skin using an RF electromagnetic energy delivery device. However, the manner (and specifically, the protocol) in which the RF is transmitted to the region of interest is highly important. Some methods will have no effect and others may have the opposite effect.

U.S. Pat. Appl. 20100016850 discloses an invention that demonstrates that application of electrical currents of about 1 milliampere, and voltages greater than 4V have a much greater esthetic effect on the skin than application of lower currents and voltages known in the prior art. This application further discloses that simultaneous application of electrical currents on the skin yields better esthetic results.

All of the RF devices known in the prior art irradiate the tissue with RF energy that has a single phase. This means of irradiation is relatively inefficient, because the waveform necessarily passes through zero twice per cycle; that is, there will inevitably be periods of irradiation during which no energy is being transferred to the skin.

Thus, means for providing RF (or in general, any kind of energy) to the region of treatment (e.g., the skin) in which an essentially continuous transfer of the energy (e.g., the RF) to the skin remains a long-felt, yet unmet, need.

SUMMARY OF THE INVENTION

The present invention is designed to meet this long-felt need. The present invention discloses a device for skin rejuvenation, adapted to apply any energy according to a predetermined protocol.

Specifically, the present invention discloses a device for skin rejuvenation, adapted to apply RF energy to the skin that comprises a plurality of pairs of RF electrodes in which each pair of electrodes transmits RF energy shifted in phase relative to the other pairs of electrodes. By this means, an essentially constant amount of RF energy can be transmitted to the skin while maintaining the benefits of RF irradiation discussed above. However, it should be pointed out that any Energy could be applied (e.g., acoustic energy, ultrasound, light, laser, electrical energy, magnetic field and any combination thereof).

It is therefore an object of the present invention to disclose a device for improving the cosmetic appearance of the skin, comprising (a) N pairs of RF electrodes, each of said pairs in independent communication with said RF generating means, said RF electrodes configured to transmit RF energy to said skin; (b) RF generating means for generating N independent RF signals of predetermined waveforms, frequencies, amplitudes, and relative phases; (c) control means for controlling the output of said RF generating means, said control means in communication with said RF generating means; and, (d) an electrically insulating casing adapted to hold said RF electrodes such that said RF electrodes may be placed in simultaneous physical contact with said skin. It is within the essence of the invention wherein said N independent RF signals are phase shifted relative to one another.

It is a further object of this invention to disclose such a device, wherein the time-dependent amplitude $A_{t,m}$ of the mth of said N independent RF signals is given by the relationship $A_{t,m}=A_{0,m} \cdot F_m(\omega_m t+\phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth RF signal.

It is a further object of this invention to disclose such a device, wherein for each of said N independent RF signals, $\phi_m=\pi k(j-1)/N$, where $0 \leq k \leq 1$ and m=1, 2, 3 ... N, j=1, 2, 3 ...; where N is the number of said pairs of electrodes. For example, for one electrode k=1, N=4 and the phase is 135 degrees and for another electrode the phase will be 45 degrees, and another numbers can be combined.

It is a further object of this invention to disclose such a device, wherein $F_m$ is chosen from the group consisting of sine, cosine, tan, cotangents (cot), sawtooth wave, triangular wave, square wave, rectangular wave, trapezoidal wave, and any combination of the above.

It is a further object of this invention to disclose such a device as defined in any of the above, wherein each of said predetermined frequencies is between about 1 Hz and about 100 MHz.

It is a further object of this invention to disclose such a device as defined in any of the above, wherein said RF signals are transmitted either in a continues mode or in pulses.

It is a further object of this invention to disclose such a device, wherein, if said RF is applied in pulses, the length of said pulses is between about 0.01 micro-sec and about 1 ms.

It is a further object of this invention to disclose such a device as defined in any of the above, additionally comprising means adapted to apply Pulsed Electromagnetic Field Therapy (PEMF).

It is a further object of this invention to disclose such a device, wherein the length of said PEMF is between about 0.1 ms and about 1000 ms.

It is a further object of this invention to disclose such a device as defined in any of the above, further comprising temperature measuring means adapted to measure the temperature of the surface of said skin.

It is a further object of this invention to disclose such a device, wherein said temperature measuring means comprises at least one sensor chosen from the group consisting of impedance meter adapted to measure impedance across at least one of said pairs of RF electrodes; thermal sensor; thermometer; and any combination thereof.

It is a further object of this invention to disclose such a device, wherein said control means are programmed to regulate the amount of RF energy transmitted to said skin such that the temperature of said skin remains within a predetermined range.

It is a further object of this invention to disclose such a device, wherein said predetermined range is between ambient temperature and 42° C.

It is a further object of this invention to disclose such a device, wherein said predetermined range is between ambient temperature and 50° C.

It is a further object of this invention to disclose such a device, wherein said predetermined range is between 30° C. and 100° C.

It is a further object of this invention to disclose such a device as defined in any of the above, wherein said electrodes are disposed about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

It is a further object of this invention to disclose such a device as defined in any of the above, wherein the power transmitted by said RF electrodes and said RF generating means to said skin is between 1 W and 700 W.

It is a further object of this invention to disclose such a device as defined in any of the above, wherein said cosmetic improvement is chosen from the group consisting of skin rejuvenation, reduction of the number of wrinkles, reduction of the depth of wrinkles, reduction of cellulite, skin tightening, circumferential reduction, and any combination of the above.

It is a further object of this invention to disclose such a device as defined in any of the above, further comprising cooling means adapted to cool said skin.

It is a further object of this invention to disclose such a device, wherein said cooling means are chosen from the group consisting of a Peltier effect cooling device, irrigation with cool water, and means for blowing air across the skin.

It is a further object of this invention to disclose such a device as defined in any of the above, wherein said RF electrodes are further adapted to provide heat to said skin.

It is a further object of this invention to disclose such a device as defined in any of the above, further comprising a deep tissue diathermy device.

It is a further object of this invention to disclose such a device, wherein said deep tissue diathermy device is chosen from the group consisting of any devices emitting RF radiation and any other means adapted for producing electrical current absorbed by subcutaneous tissue.

It is a further object of this invention to disclose such a device, wherein said deep tissue diathermy device further comprises (a) at least one electrical output device adapted to generate RF electromagnetic energy; and (b) at least two electrodes electrically coupled to said electrical output device and placed on said skin region, wherein all said electrodes are adapted to simultaneously apply said RF energy to said skin.

It is a further object of this invention to disclose such a device, wherein said deep tissue diathermy device further comprises (a) at least one electrical output device adapted to generate electrical current; (b) at least two electrodes electrically coupled to said electrical output device and placed on said skin region, wherein all of said electrodes are adapted to simultaneously apply said electrical current to said skin.

It is a further object of this invention to disclose such a device, wherein said deep tissue diathermy device is chosen from the group consisting of acoustic (e.g., ultrasonic) diathermy devices, optical diathermy devices, electromagnetic induction diathermy devices, devices for producing sound waves, ultrasonic diathermy devices, and devices for direct application of heat.

It is a further object of this invention to disclose such a device, wherein said deep tissue diathermy device is an optical device adapted to emit light in wavelengths absorbed by subcutaneous tissue such that said subcutaneous tissue is heated.

It is a further object of this invention to disclose such a device, wherein said deep tissue diathermy device is a device for producing sound waves adapted to emit sound waves of a frequency absorbed by the subcutaneous tissue such that said subcutaneous tissue is heated.

It is a further object of this invention to disclose such a device, wherein said control means are adapted to monitor physical tissue parameters and to change at least one of (a) the amount of heat applied and (b) the form of said RF in response to the values of said physical tissue parameters.

It is a further object of this invention to disclose such a device, wherein said control means further comprise (a) processing means adapted to store in a communicable database predetermined parameters defining safe and unsafe treatment parameters, said parameters chosen from the group consisting of time of said treatment, the temperature of said skin, frequency, power, energy applied by said RF generating means, depth to which said device operates, magnetic field intensity, tissue impedance, specific absorption rate, superficial muscle contractions and any combination thereof (b) sensing means adapted to sense electromagnetic radiation and heat radiation parameters chosen from a group consisting of time of said treatment, temperature of said tissue, frequency, power, intensity of ultrasound irradiation, energy applied by said RF generating means, depth to which said device operates, magnetic field intensity, tissue impedance, specific absorption rate, superficial muscle contractions and any combination thereof; and (c) regulating means adapted to stop the operation of said device if said parameters are determined to be unsafe.

It is a further object of this invention to disclose such a device as defined in any of the above, wherein said control means additionally comprise a feedback mechanism, adapted to change said RF signal according to predetermined medical needs, and comprising (a) sensing means adapted to monitor electrotherapy parameters related to the level of skin rejuvenation and viability; (b) processing means, adapted to determine the degree of esthetic improvement in at least one tissue parameter related to the level of skin rejuvenation and vitality; and (c) regulating means adapted to stop the operation of said device when said degree of esthetic improvement reaches a predetermined value.

It is a further object of this invention to disclose such a device, wherein said electrotherapy parameters are chosen from the group consisting of dermal tensile forces, tissue impedance, muscle contraction forces, skin elasticity, and any combination thereof.

It is a further object of this invention to disclose such a device, wherein said at least one tissue parameter is chosen from the group consisting of dermal tensile forces, tissue impedance, muscle contraction forces, skin elasticity, and any combination thereof.

It is a further object of this invention to disclose such a device, wherein said sensing means are adapted to sense electrotherapy parameters are chosen from the group consisting of time of said treatment, temperature of said tissue, frequency, power, tissue impedance, superficial muscle contractions and any combination thereof.

It is a further object of this invention to disclose such a device, wherein said processing means are adapted to store in a communicable database predetermined parameters defining safe and unsafe treatment conditions.

It is a further object of this invention to disclose such a device, wherein said predetermined parameters are chosen from the group consisting of time of said treatment, temperature of said tissue, frequency, power, tissue impedance, superficial muscle contractions, and any combination thereof.

It is a further object of this invention to disclose such a device as defined in any of the above, additionally comprising means for massaging said skin.

It is a further object of this invention to disclose such a device as defined in any of the above, wherein at least one of said RF electrodes comprises a hypodermic syringe for penetrating into subcutaneous tissue.

It is a further object of this invention to disclose a method for providing cosmetic improvement to the skin, comprising (a) providing (i) N pairs of RF electrodes, each of said pairs in independent communication with RF generating means, said RF electrodes configured to transmit RF energy to said skin; (ii) RF generating means for generating N independent RF signals of predetermined waveforms, frequencies, amplitudes, and relative phases; (iii) control means for controlling the output of said RF generating means, said control means in communication with said RF generating means;

(b) generating N independent RF signals of predetermined waveforms, frequencies, amplitudes, and relative phases; (c) transmitting each of said N independent RF signals to a pair of electrodes; (d) placing said electrodes in physical contact with said skin; and (d) transmitting energy carried by said RF signals to said skin. It is within the essence of the invention wherein said N independent RF signals are phase-shifted relative to one another.

It is a further object of this invention to disclose such a method, wherein said step of generating N independent RF signals further comprises generating N independent RF signals such that the time-dependent amplitude $A_{t,m}$ of the mth of said N independent RF signals is given by the relationship $A_{t,m}=A_{0,m} \cdot F_m(\omega_m t+\phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth RF signal.

It is a further object of this invention to disclose such a method, further comprising a step of providing said phase shift $\phi_m$ for each of said N independent RF signals according to the relationship $\phi_m=\pi k(j-1)/N$, where $0 \leq k \leq 1$, m=1, 2, 3 . . . N and j=1, 2, 3 . . . ; where N is the number of said pairs of electrodes.

It is a further object of this invention to disclose such a method, further comprising a step of choosing $F_m$ from the group consisting of sine, cosine, tan, cotangents (cot), sawtooth wave, triangular wave, square wave, rectangular wave, trapezoidal wave, and any combination of the above.

It is a further object of this invention to disclose such a method as defined in any of the above, wherein said step of generating N independent RF signals of predetermined waveforms, frequencies, amplitudes, and relative phases comprises a step of generating N independent RF signals with frequencies between about 1 Hz and about 100 MHz.

It is a further object of this invention to disclose such a method as defined in any of the above, further comprising a step of transmitting said RF signals either in a continues node or in pulses.

It is a further object of this invention to disclose such a method, wherein, when the RF is applied in pulses, the length of said pulses is between about 0.01 micro-sec and about 1 ms.

It is a further object of this invention to disclose such a method as defined in any of the above, additionally comprising means adapted to apply Pulsed Electromagnetic Field Therapy (PEMF).

It is a further object of this invention to disclose such a method, wherein said step of transmitting said PEMF signals in pulses further comprises transmitting said pulses with pulse lengths of between about 0.1 and about 1000 ms.

It is a further object of this invention to disclose such a method as defined in any of the above, further comprising a step of measuring the temperature of the surface of said skin.

It is a further object of this invention to disclose such a method, wherein said step of measuring the temperature of the surface of said skin further comprises measuring the temperature of the surface of said skin by means of at least one sensor chosen from the group consisting of impedance meter adapted to measure impedance across at least one of said pairs of RF electrodes; thermal sensor; thermometer; and any combination thereof.

It is a further object of this invention to disclose such a method, further comprising a step of regulating the amount of RF energy transmitted to said skin such that the temperature of said skin remains within a predetermined range.

It is a further object of this invention to disclose such a method, wherein said step of regulating the amount of RF energy transmitted to said skin further comprises regulating the amount of RF energy transmitted to said skin such that the temperature of said skin remains between ambient temperature and 37° C.

It is a further object of this invention to disclose such a method, wherein the temperature of said skin remains between ambient temperature and 50° C.

It is a further object of this invention to disclose such a method, wherein the temperature of said skin remains between 30° C. and 100° C.

It is a further object of this invention to disclose such a method, wherein said step of regulating the amount of RF energy transmitted to said skin further comprises regulating the amount of RF energy transmitted to said skin such that the temperature of said skin remains between 30° C. and 80° C.

It is a further object of this invention to disclose such a method as defined in any of the above, further comprising a step of disposing said electrodes within an electrically insulating casing.

It is a further object of this invention to disclose such a method, further comprising a step of disposing about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

It is a further object of this invention to disclose such a method as defined in any of the above, further comprising a step of transmitting to said skin a power of between 1 W and 700 W by said RF electrodes and said RF generating means.

It is a further object of this invention to disclose such a method as defined in any of the above, further comprising a step of providing a cosmetic/esthetic improvement to the skin chosen from the group consisting of skin rejuvenation, reduction of the number of wrinkles, reduction of the depth of wrinkles, reduction of cellulite, skin tightening, circumferential reduction, and any combination of the above.

It is a further object of this invention to disclose such a method as defined in any of the above, further comprising a step of cooling said skin.

It is a further object of this invention to disclose such a method, wherein said step of cooling said skin further comprises cooling said skin by the use of means chosen from the group consisting of a Peltier effect cooling device, irrigation with cool water, and means for blowing air across the skin.

It is a further object of this invention to disclose such a method as defined in any of the above, further comprising a step of heating said skin by means of said RF electrodes.

It is a further object of this invention to disclose such a method as defined in any of the above, further comprising a step of performing deep tissue diathermy.

It is a further object of this invention to disclose such a method, wherein said step of performing deep tissue diathermy further comprises performing deep tissue diathermy by a method chosen from the group consisting of emitting RF radiation and producing electrical current absorbed by subcutaneous tissue.

It is a further object of this invention to disclose such a method, wherein said step of performing deep tissue diathermy further comprises (a) generating RF electromagnetic energy by use of at least one electrical output device; (b) coupling at least two electrodes to said at least one electrical output device; and (c) applying simultaneously said RF energy to said skin.

It is a further object of this invention to disclose such a method, wherein said step of performing deep tissue diathermy further comprises (a) generating electrical current by means of at least one electrical output; (b) coupling electrically at least two electrodes electrically to said electrical output; (c) placing said electrodes on said skin; and (d) applying simultaneously said electrical current to said skin.

It is a further object of this invention to disclose such a method, wherein said step of performing deep tissue diathermy further comprises performing deep tissue diathermy by a means chosen from the group consisting of ultrasonic diathermy devices, optical diathermy devices, electromagnetic induction diathermy devices, devices for producing sound waves, ultrasonic diathermy devices, and devices for direct application of heat.

It is a further object of this invention to disclose such a method, wherein said step of performing deep tissue diathermy further comprises performing deep tissue diathermy by means of an optical device adapted to emit light in wavelengths absorbed by subcutaneous tissue such that said subcutaneous tissue is heated.

It is a further object of this invention to disclose such a method, wherein said step of performing deep tissue diathermy further comprises performing deep tissue diathermy by means of a device for producing sound waves adapted to emit sound waves of a frequency absorbed by the subcutaneous tissue such that said subcutaneous tissue is heated.

It is a further object of this invention to disclose such a method, further comprising steps of (a) monitoring physical tissue parameters; and (b) changing at least one of (i) the amount of heat applied and (ii) the form of said RF in response to the values of said physical tissue parameters.

It is a further object of this invention to disclose such a method, further comprising steps of (a) storing in a communicable database predetermined parameters defining safe and unsafe treatment parameters, said parameters chosen from the group consisting of time of said treatment, the temperature of said skin, frequency, power, energy applied by said RF generating means, depth to which said device operates, magnetic field intensity, tissue impedance, specific absorption rate, superficial muscle contractions and any combination thereof; (b) sensing electromagnetic radiation and heat radiation parameters chosen from a group consisting of time of said treatment, temperature of said tissue, frequency, power, intensity of ultrasound irradiation, energy applied by said RF generating means, depth to which said device operates, magnetic field intensity, tissue impedance, specific absorption rate, superficial muscle contractions and any combination thereof; and (c) ceasing the continued performance of said method if said parameters are determined to be unsafe.

It is a further object of this invention to disclose such a method as defined in any of the above, further comprising steps of (a) monitoring electrotherapy parameters related to the level of skin rejuvenation and viability; (b) determining the degree of esthetic improvement in at least one tissue parameter related to the level of skin rejuvenation and vitality; and (c) ceasing the continued performance of said method when said degree of esthetic improvement reaches a predetermined value.

It is a further object of this invention to disclose such a method, wherein said step of monitoring electrotherapy parameters further comprises monitoring at least one parameter chosen from the group consisting of dermal tensile forces, tissue impedance, muscle contraction forces, and skin elasticity.

It is a further object of this invention to disclose such a method, wherein said step of determining the degree of esthetic improvement in at least one tissue parameter related to the level of skin rejuvenation and vitality further comprises a of determining the degree of esthetic improvement in at least one parameter chosen from the group consisting of dermal tensile forces, tissue impedance, muscle contraction forces, and skin elasticity.

It is a further object of this invention to disclose such a method, further comprising a step of monitoring electrotherapy parameters chosen from the group consisting of time of said treatment, temperature of said tissue, frequency, power, tissue impedance, superficial muscle contractions and any combination thereof.

It is a further object of this invention to disclose such a method, further comprising a step of storing in a communicable database predetermined parameters defining safe and unsafe treatment conditions.

It is a further object of this invention to disclose such a method, wherein said step of storing in a communicable database predetermined parameters defining safe and unsafe treatment conditions further comprises storing in a communicable database at least one parameters chosen from the group consisting of time of said treatment, temperature of said tissue, frequency, power, tissue impedance, and superficial muscle contractions.

It is a further object of this invention to disclose such a method as defined in any of the above, further comprising a step of massaging said skin.

It is a further object of this invention to disclose such a method as defined in any of the above, further comprising a step of incorporating a hypodermic syringe for penetrating into subcutaneous tissue into at least one of said electrodes.

It is another object of the present invention to provide a device for improving the cosmetic/esthetic appearance of the skin, comprising:
- N pairs of electrodes, each of said pairs in independent communication with energy generating means, said electrodes configured to transmit said energy to said skin;
- energy generating means for generating N independent energy signals of predetermined waveforms, frequencies, amplitudes, and relative phases;
- control means for controlling the output of said energy generating means, said control means in communication with said energy generating means; and,
- an electrically insulating casing adapted to hold said electrodes such that said electrodes may be placed in simultaneous physical contact with said skin; wherein said N independent energy signals are phase shifted relative to one another.

It is another object of the present invention to provide the device as defined above, wherein the time-dependent amplitude $A_{t,m}$ of the mth of said N independent energy signals is given by the relationship $A_{t,m}=A_{0,m}\cdot F_m(\omega_m t+\phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth energy signal It is another object of the present invention to provide the device as defined above, wherein for each of said N independent energy signals, $\phi_m=\pi k(j-1)/N$, where $0 \le k \le 1$, m=1, 2, 3 ... N and j=1, 2, 3 ... ; where N is the amount of said electrodes pairs.

It is another object of the present invention to provide the device as defined above, wherein $F_m$ is chosen from the group consisting of sine, cosine, tan, cotangents (cot), sawtooth wave, triangular wave, square wave, rectangular wave, trapezoidal wave, and any combination of the above.

It is another object of the present invention to provide the device as defined above, wherein said energy is selected from a group consisting of ultrasound, light, laser, electrical energy, magnetic field and any combination thereof.

It is another object of the present invention to provide the device as defined above, wherein said N output signals are transmitted in either continues mode or in pulses.

It is a further object of this invention to disclose such a device, wherein, when the RF is applied in pulses, the length of said pulses is between about 0.01 micro-sec and about 1 ms.

It is a further object of this invention to disclose such a device as defined in any of the above, additionally comprising means adapted to apply Pulsed Electromagnetic Field Therapy (PEMF).

It is another object of the present invention to provide the device as defined above, wherein the length of said PEMF is between about 0.1 ms and about 1000 ms.

It is another object of the present invention to provide the device as defined above, further comprising temperature measuring means adapted to measure the temperature of the surface of said skin.

It is another object of the present invention to provide the device as defined above, wherein said temperature measuring means comprises at least one sensor chosen from the group consisting of impedance meter adapted to measure impedance across at least one of said pairs of RF electrodes; thermal sensor; thermometer; and any combination thereof.

It is another object of the present invention to provide the device as defined above, further comprising control means; wherein said control means are programmed to regulate the amount of energy transmitted to said skin such that the temperature of said skin remains within a predetermined range.

It is another object of the present invention to provide the device as defined above, wherein said predetermined range is between ambient temperature and 42° C.

It is a further object of this invention to disclose such a device, wherein said predetermined range is between ambient temperature and 50° C.

It is a further object of this invention to disclose such a device, wherein said predetermined range is between 30° C. and 100° C.

It is another object of the present invention to provide the device as defined above, wherein said electrodes are disposed about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

It is another object of the present invention to provide the device as defined above, wherein the power transmitted by said device to said skin is between 1 and 700 W.

It is another object of the present invention to provide the device as defined above, wherein said cosmetic improvement is chosen from the group consisting of skin rejuvenation, reduction of the number of wrinkles, reduction of the depth of wrinkles, reduction of cellulite, skin tightening, circumferential reduction, and any combination of the above.

It is another object of the present invention to provide the device as defined above, further comprising cooling means adapted to cool said skin.

It is another object of the present invention to provide the device as defined above, wherein said cooling means are chosen from the group consisting of a Peltier effect cooling device, irrigation with cool water, and means for blowing air across the skin.

It is another object of the present invention to provide the device as defined above, wherein said energy is adapted to provide heat to said skin.

It is another object of the present invention to provide the device as defined above, further comprising a deep tissue diathermy device.

It is another object of the present invention to provide the device as defined above, wherein said deep tissue diathermy device is chosen from the group consisting of any devices emitting RF radiation and any other means adapted for producing electrical current absorbed by subcutaneous tissue.

It is another object of the present invention to provide the device as defined above, wherein said deep tissue diathermy device further comprises:
- at least one electrical output device adapted to generate RF electromagnetic energy; and,
- at least two electrodes electrically coupled to said electrical output device and placed on said skin region, wherein all said electrodes are adapted to simultaneously apply said RF energy to said skin.

It is another object of the present invention to provide the device as defined above, wherein said deep tissue diathermy device further comprises:
- at least one electrical output device adapted to generate electrical current; and,
- at least two electrodes electrically coupled to said electrical output device and placed on said skin region, wherein all of said electrodes are adapted to simultaneously apply said electrical current to said skin.

It is another object of the present invention to provide the device as defined above, wherein said deep tissue diathermy device is chosen from the group consisting of acoustic (e.g., ultrasonic) diathermy devices, optical diathermy devices, electromagnetic induction diathermy devices, devices for producing sound waves, ultrasonic diathermy devices, and devices for direct application of heat.

It is another object of the present invention to provide the device as defined above, wherein said deep tissue diathermy device is an optical device adapted to emit light in wavelengths absorbed by subcutaneous tissue such that said subcutaneous tissue is heated.

It is another object of the present invention to provide the device as defined above, wherein said deep tissue diathermy device is a device for producing sound waves adapted to emit sound waves of a frequency absorbed by the subcutaneous tissue such that said subcutaneous tissue is heated.

It is another object of the present invention to provide the device as defined above, additionally comprising control means; wherein said control means additionally comprise a feedback mechanism, adapted to change said energy signal according to predetermined medical needs, and comprising:
- sensing means adapted to monitor electrotherapy parameters related to the level of skin rejuvenation and viability;
- processing means, adapted to determine the degree of esthetic improvement in at least one tissue parameter related to the level of skin rejuvenation and vitality; and,
- regulating means adapted to stop the operation of said device when said degree of esthetic improvement reaches a predetermined value.

It is another object of the present invention to provide the device as defined above, wherein said electrotherapy parameters are chosen from the group consisting of dermal tensile forces, tissue impedance, muscle contraction forces, skin elasticity, and any combination thereof.

It is another object of the present invention to provide the device as defined above, wherein said at least one tissue parameter is chosen from the group consisting of dermal tensile forces, tissue impedance, muscle contraction forces, skin elasticity, and any combination thereof.

It is another object of the present invention to provide the device as defined above, wherein said sensing means are adapted to sense electrotherapy parameters are chosen from the group consisting of time of said treatment, temperature of said tissue, frequency, power, tissue impedance, superficial muscle contractions and any combination thereof.

It is another object of the present invention to provide the device as defined above, wherein said processing means are adapted to store in a communicable database predetermined parameters defining safe and unsafe treatment conditions.

It is another object of the present invention to provide the device as defined above, wherein said predetermined parameters are chosen from the group consisting of time of said treatment, temperature of said tissue, frequency, power, tissue impedance, superficial muscle contractions, and any combination thereof.

It is another object of the present invention to provide the device as defined above, additionally comprising means for massaging said skin.

BRIEF DESCRIPTION OF THE DRAWINGS

The invention will now be described with reference to the drawings, wherein.

DETAILED DESCRIPTION OF THE PREFERRED EMBODIMENTS

Figure 1:
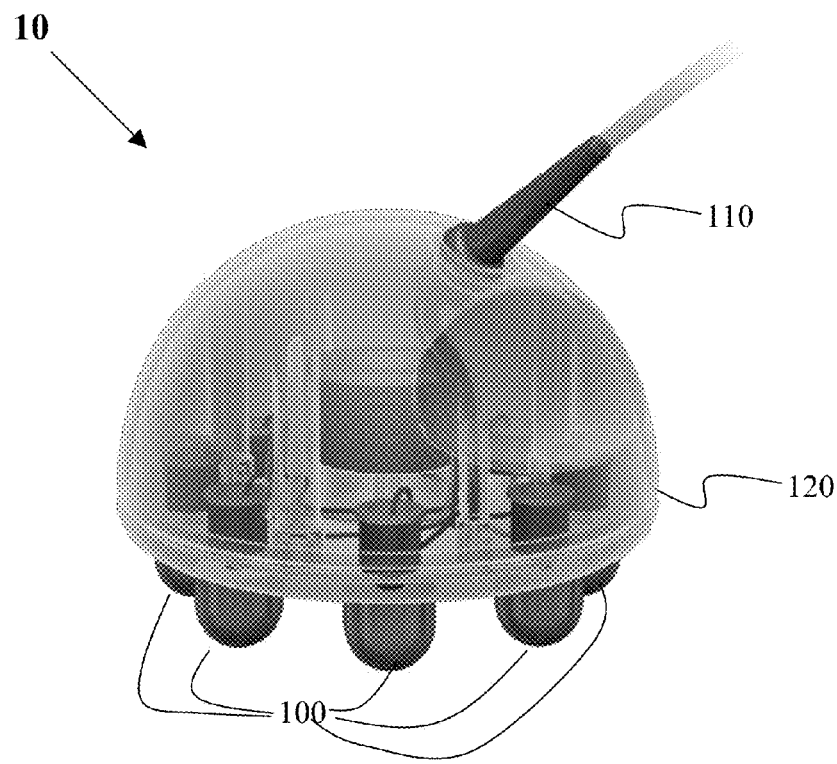
FIG. 1 presents a schematic view of one embodiment of the invention herein disclosed.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

With respect to parameters that characterize the invention disclosed herein and the cosmetic treatment effected thereby, "unsafe" parameters are understood to be parameters that will cause tissue damage or excessive discomfort to the person undergoing treatment, e.g. overheating, transmitting energy to tissue layers below the skin, etc. According to one embodiment, the device of the present invention automatically prevents the parameters from reaching the unsafe zone and maintains the same within the safe zone.

The invention comprises a novel device for improving the cosmetic appearance of the skin, which is described in detail below. In preferred embodiments of the invention, the cosmetic improvement achieved includes at least one of skin rejuvenation; reduction in the number of wrinkles; reduction of the depth of wrinkles; reduction of cellulite; skin tightening; circumferential reduction.

The present invention provides a device for improving the cosmetic appearance of the skin, comprising:
- N pairs of electrodes, each of said pairs in independent communication with energy generating means, said electrodes configured to transmit said energy to said skin;
- energy generating means for generating N independent energy signals of predetermined waveforms, frequencies, amplitudes, and relative phases;
- control means for controlling the output of said energy generating means, said control means in communication with said energy generating means; and,
- an electrically insulating casing adapted to hold said electrodes such that said electrodes may be placed in simultaneous physical contact with said skin;
- wherein said N independent energy signals are phase shifted relative to one another.

As an example, the present invention further provides a device for skin rejuvenation, adapted to apply RF energy to the skin that comprises a plurality of pairs of RF electrodes in which each pair of electrodes transmits RF energy shifted in phase relative to the other pairs of electrodes. By this means, an essentially constant amount of RF energy can be transmitted to the skin while maintaining the benefits of RF irradiation discussed above.

Yet more, it is an object of the present invention to disclose the device as disclosed above, wherein the energy emitted is RF energy.

Thus, it is another object of the present invention to provide a device for improving the cosmetic appearance of the skin, comprising (a) N pairs of RF electrodes, each of said pairs in independent communication with said RF generating means, said RF electrodes configured to transmit RF energy to said skin; (b) RF generating means for generating N independent RF signals of predetermined waveforms, frequencies, amplitudes, and relative phases; (c) control means for controlling the output of said RF generating means, said control means in communication with said RF generating means; and, (d) an electrically insulating casing adapted to hold said RF electrodes such that said RF electrodes may be placed in simultaneous physical contact with said skin. It is within the essence of the invention wherein said N independent RF signals are phase shifted relative to one another.

It is a further object of this invention to disclose such a device, wherein the time-dependent amplitude $A_{t,m}$ of the mth of said N independent RF signals is given by the relationship $A_{t,m}=A_{0,m} \cdot F_m(\omega_m t + \phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth RF signal.

It is a further object of this invention to disclose such a device, wherein for each of said N independent RF signals, $\phi_m = \pi k(j-1)/N$, where $0 \leq k \leq 1$, m=1, 2, 3 . . . N and j=1, 2, 3 . . . ; where N is the number of said pairs of electrodes.

The following description is provided to the application of RF energy, however it is to be emphasized that the following method can be applied to any type of energy and it is not limited to the application of merely RF.

Reference is now made to FIG. 1, which presents a schematic view (not to scale) of one embodiment 10 of the device disclosed in the present invention. The embodiment comprises a plurality of N pairs of electrodes (i.e. a total of 2N electrodes) 100. The electrodes are in communication 110 with a source of RF radiation, which is in communication with control means for controlling the output of the RF source. Both the RF source and control means are not shown in the figure. Any suitable means known in the art for production of RF radiation and control of the resulting RF output may be used. While the means for communication shown in FIG. 1 incorporate a hardwired connection, any appropriate means of communication with the RF source, including wireless communication means, may be used. The electrodes are configured to transmit RF radiation received from the RF source to the skin undergoing cosmetic treatment. The electrodes and electrical connections are enclosed within a casing 120 that is made of electrically non-conducting material such as, for example, plastic. In preferred embodiments, the electrodes are disposed about the distal end of the casing such that all of the electrodes may be placed simultaneously in physical contact with the skin undergoing cosmetic treatment. While in preferred embodiments, the electrodes are disposed about the circumference of a circle, the actual geometrical arrangement of the electrodes may be any suitable arrangement; non-limiting examples include linear, zigzag, on the perimeter and/or within the area of a substantially polygonal, circular, oval, or irregular shape, or any combination of the above.

In order to ensure the user's safety, in preferred embodiments of the invention, the device is adapted to operate according to a medical electrical equipment standard chosen from the group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 and any combination thereof.

Figure 2:
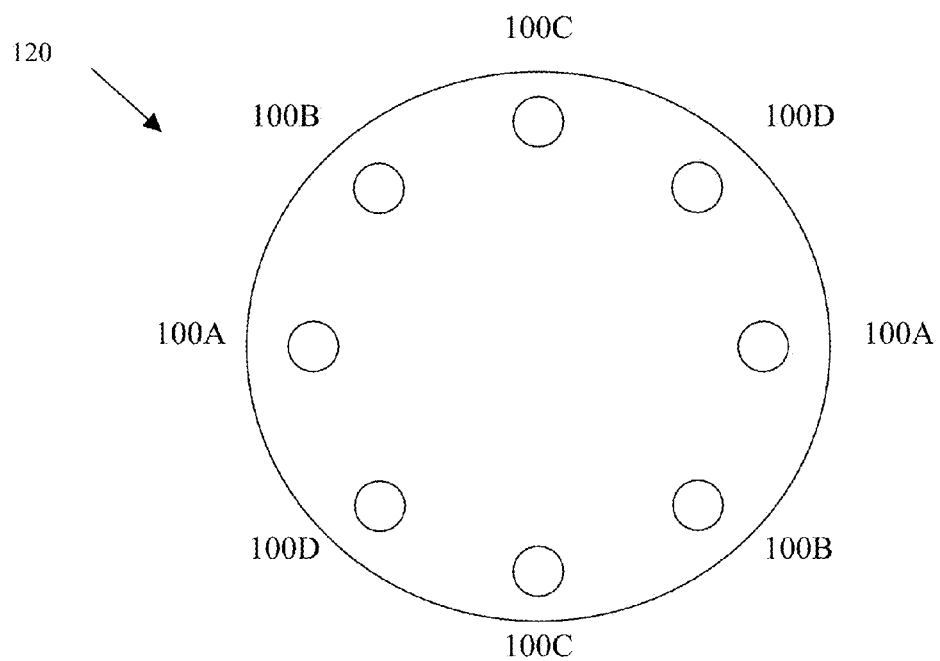
FIG. 2 presents a face-on schematic view of the electrodes according to one embodiment of the invention herein disclosed.

Reference is now made to FIG. 2, which shows a schematic (not to scale) face-on view of an arrangement of electrodes on the face of the distal portion of casing 120 according to one embodiment of the invention. In this embodiment, the electrodes 100 are arranged about the circumference of a circle, and N=4 (N is the number of pairs of electrodes). The four pairs of electrodes, where each pair comprises electrodes connected by a diameter of the circle, are labeled A, B, C, and D.

The RF generating means comprises means for producing N independent RF signals of predetermined waveforms, frequencies, amplitudes, and relative phases (it should be noted that N is also the number of pairs of electrodes). Means for production of RF signals with several independent output channels are well-known in the art. In preferred embodiments, the waveforms, frequencies, and amplitudes are chosen to be those that are most effective for skin treatment. In preferred embodiments, the frequencies of the RF signals are between about 1 Hz and about 100 MHz, and the power transmitted by said RF electrodes and said RF generating means to the skin undergoing cosmetic treatment is between 1 W and 700 W.

The RF output may be continuous wave or pulsed. In preferred embodiments in which the RF output is pulsed, the pulses have duration of between about 0.01 micro-sec and about 1 ms. However, it should be pointed that the RF can be applied in a continues mode.

According to another embodiment of the present invention, there are provided means adapted to apply Pulsed Electromagnetic Field Therapy (PEMF). In preferred embodiments in which the RF output is pulsed, the pulses have duration of between about 0.1 ms and about 1000 MS.

Uniquely to the invention disclosed herein relative to devices and methods known in the art, the N independent RF signals are phase-shifted relative to one another. The time dependent amplitude $A_{t,m}$ of the mth RF signal is thus given according to the relation $A_{t,m}=A_{0,m} \cdot F_m(\omega_m t + \phi_m)$, where $A_{0,m}$ is a normalization constant (which is greater than or equals to 1), $F_m$ is a periodic function of time, $\omega_m$ is the angular frequency of the mth signal, and $\phi_m$ is the phase shift of the mth signal. Note that while in preferred embodiments of the invention, $A_{0,m}$, $F_m$, and $\omega_m$ are the same for all N signals (it should be noted that N is greater than or equals 1), and the phase shift between successive signals is the same, embodiments in which any or all of these parameters vary for the different signals are contemplated by the inventor as being within the scope of the invention. In preferred embodiments, $F_m$ is chosen from sine, cosine, square wave, triangular wave, trapezoidal wave, sawtooth, and any combination thereof. In embodiments in which the relative phase shifts from signal to signals are equal, $\phi_m$ for the mth signal of the N is given by the relation $\phi_m = \pi k(j-1)/N$, where $0 \leq k \leq 1$, m=1, 2, 3 . . . N and j=1, 2, 3 . . . ; where N is the number of said pairs of electrodes.

Reference is now made to FIG. 3, which presents graphical representations of non-limiting examples of RF signals that may be applied to the electrode arrangement shown in FIG. 2. In these graphs, the normalized amplitude of the signal is given as a function of $\omega t$. In each graph, the curve corresponding to the signal transmitted to a particular pair of electrodes is labeled with the same letter as the corresponding pair of electrodes.

Figure 3A:
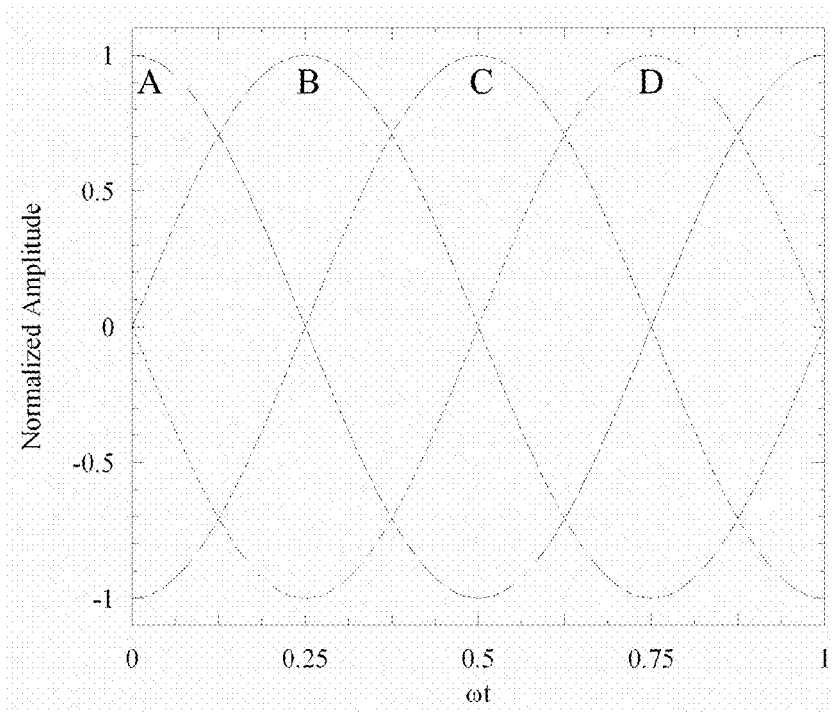
FIG. 3 presents a series of graphs illustrating the RF signal as a function of time for various embodiments of the invention; and, FIG. 4 presents a schematic view of a second embodiment of the invention herein disclosed.

FIG. 3A presents an embodiment in which N is 4, $F_m$ is a sine function, $\phi_m = \pi k(j-1)/N$ where k=1 and N=4; and $A_{0,m}$ is 1.

Figure 3B:
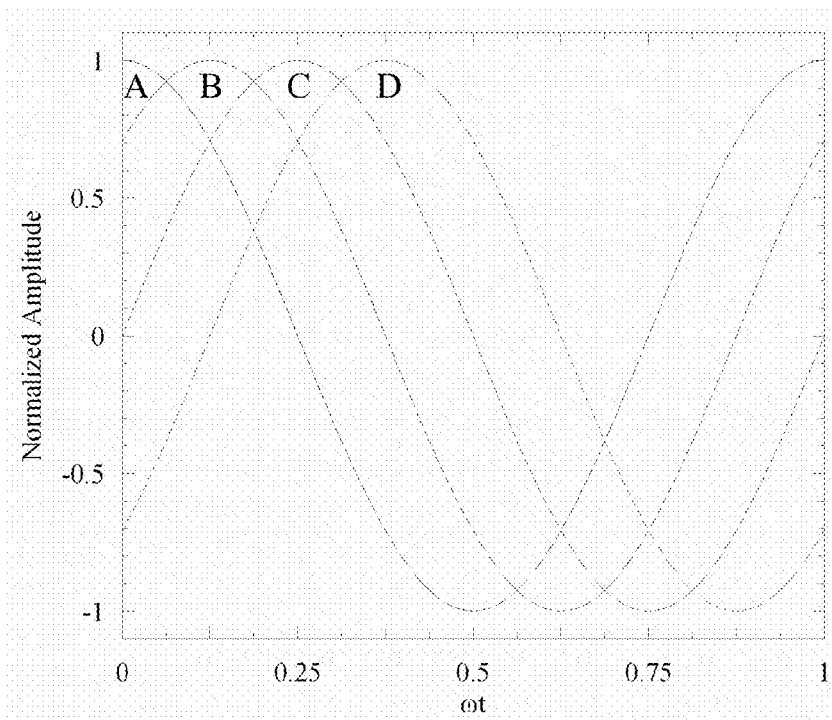

FIG. 3B presents an embodiment in which N is 4, $F_m$ is a sine function, $\phi_m = \pi k(j-1)/N$ where k=1 and N=4, and $A_{0,m}$ is 1.

Figure 3C:
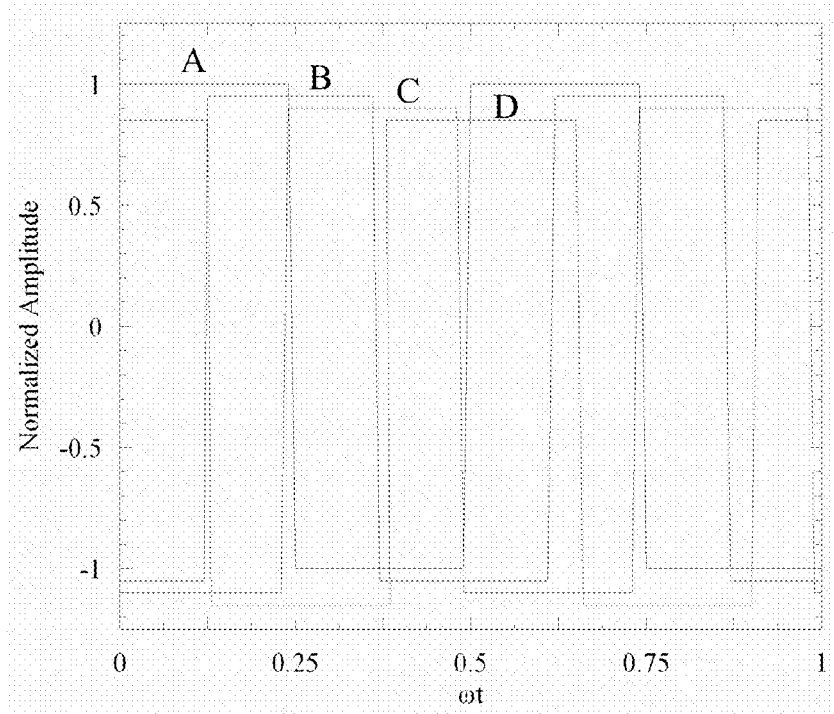

FIG. 3C presents an embodiment in which N is 4, $F_m$ is a square wave function, $\phi_m$ is $\phi_m = \pi k(j-1)/N$ where k=1 and N=4; in this case, for clarity of presentation, two cycles are shown (i.e. the x-axis is actually $2\omega t$), and the amplitudes of curves B, C, and D have been offset from 1. Thus, $A_{0,m}$ for A is 1; $A_{0,m}$ for B is 0.95, $A_{0,m}$ for C is 0.9; and, $A_{0,m}$ for D is 0.85.

Figure 3D:
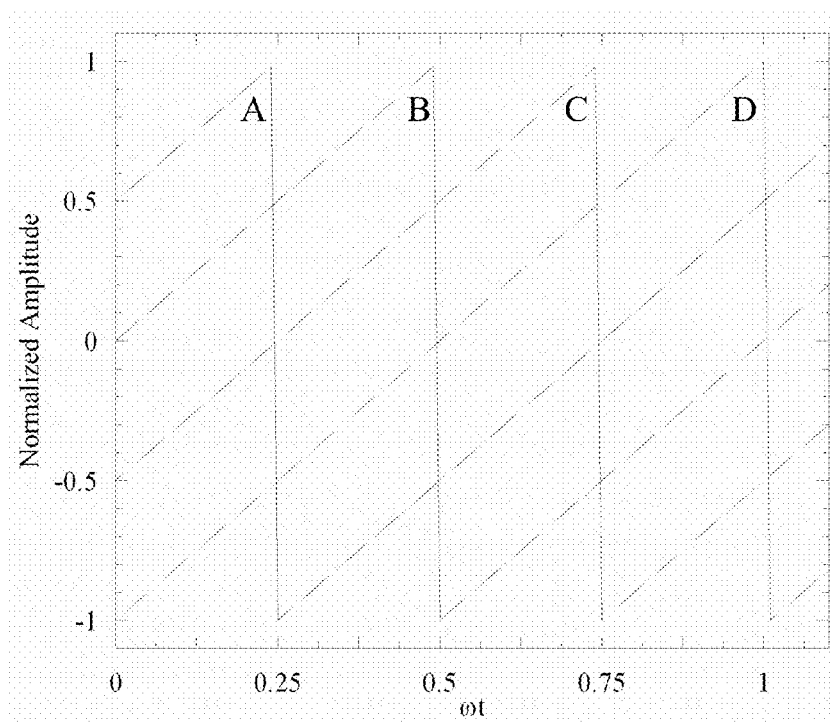

FIG. 3D presents an embodiment in which the waveform is a sawtooth function and $\phi_m = \pi k(j-1)/N$ where k=1 and N=4, and $A_{0,m}$ is 1.

In some embodiments of the device, it also comprises means for measuring the temperature of the skin being treated.

In preferred embodiments, the temperature measuring is incorporated into casing 120 and disposed in such a manner that the temperature sensor makes contact with the skin while the device is in use.

In preferred embodiments of the invention that include a temperature sensor, the sensor is chosen from the group consisting of an impedance meter adapted to measure impedance across at least one of said pairs of RF electrodes; a thermal sensor; a thermometer; and any combination thereof.

In more preferred embodiments of the invention that include a temperature sensor, control means 140 are programmed to regulate the amount of RF energy transmitted to the skin such that the temperature of the surface of the skin remains within a predetermined range.

Feedback mechanisms for raising or lowering the output of a signal generator in response to and in correlation with an input from an external sensor and means for incorporating them into control mechanisms for signal generators are well-known in the art, and any such feedback mechanism appropriate for the control means may be used. In the most preferred embodiments that include a temperature sensor, the temperature range may be (a) from ambient temperature to 42° C. or (b) between 30° C. and 100° C.

It should be noted that according to one embodiment of the present invention, the temperature sensors are embedded within the device and according to another embodiment, the temperature sensors are position on the surface of the device. According to other embodiments, the temperature sensors come in contact with the skin and according to another embodiment, the sensors are not in contact with the skin.

In other embodiments of the invention, the device incorporates cooling means adapted to cool the skin being treated. In preferred embodiments that incorporate such cooling means, the cooling means is chosen from the group consisting of wherein said cooling means are chosen from the group consisting of a Peltier effect cooling device, irrigation with cool water, and means for blowing air across the skin. The cooling means may be integrated into case 120 or applied outside of the casing either as a cooling unit attached to the casing or as a separate unit.

In yet other embodiments of the invention, the RF electrodes are further adapted to provide heat to the skin being treated.

Figure 4:
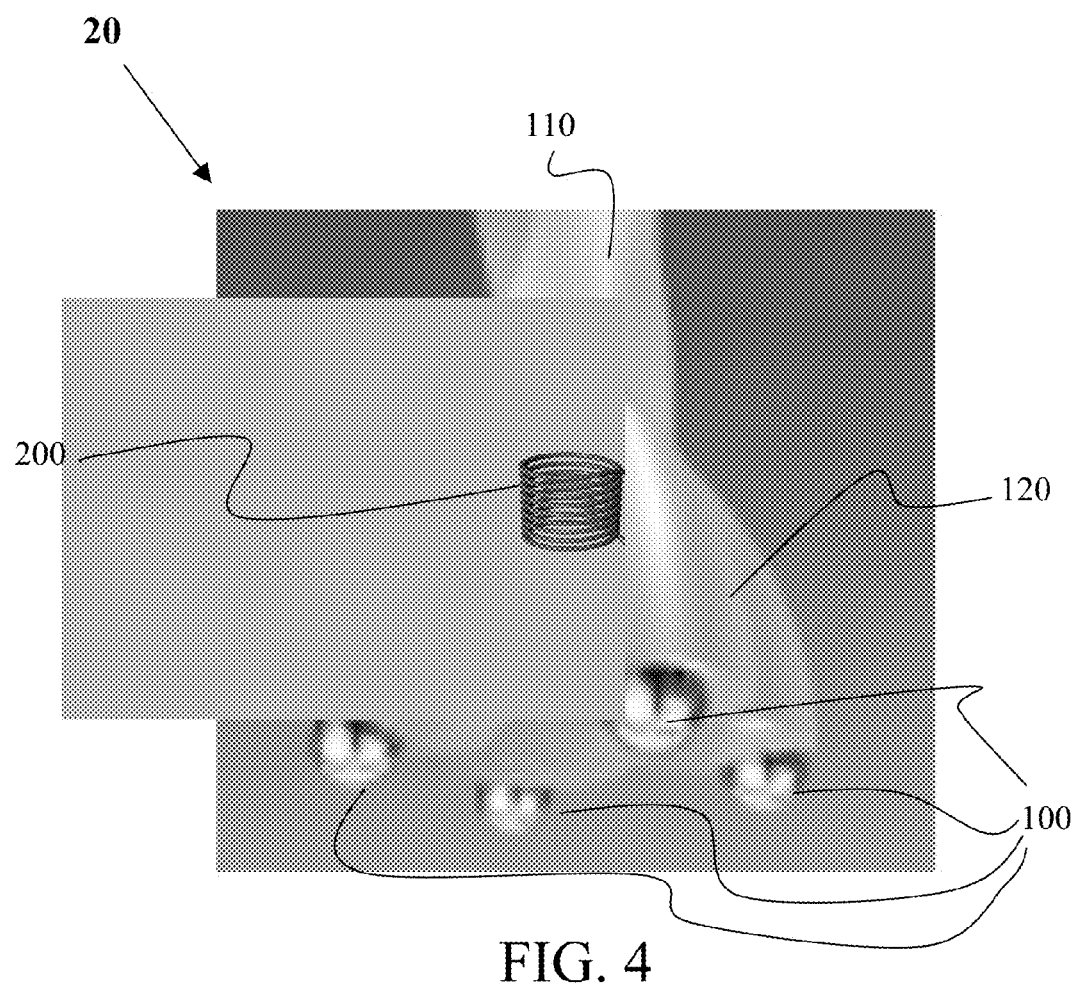

Reference is now made to FIG. 4, which presents a schematic (not to scale) illustration of one embodiment 20 of a device according to the present invention that additionally incorporates a device 200 for performing deep tissue diathermy. In preferred embodiments of the invention that include a device for performing deep tissue diathermy, the device is selected from the group consisting of any devices emitting RF radiation and any other means adapted for producing electrical current absorbed by subcutaneous tissue.

In more preferred embodiments of the invention in which a deep tissue diathermy device is incorporated, the electrodes that provide the pulsed electromagnetic field (PEMF) therapy also provide RF electrical current for the diathermy treatment. Examples of how to incorporate deep tissue diathermy devices into a device for PEMF therapy are disclosed in detail in U. S. Pat. Appl. US2011/0130618; one of ordinary skill in the art will readily understand how to apply the information disclosed in that application to the device disclosed in the present invention.

In preferred embodiments of the invention in which it incorporates a deep tissue diathermy device, the deep tissue diathermy device further incorporates at least one electrical output device adapted to generate RF electromagnetic energy; and at least two electrodes electrically coupled to said electrical output device and placed on said skin region, wherein all said electrodes are adapted to simultaneously apply said RF energy to said skin.

In more preferred embodiments of the invention in which it incorporates a deep tissue diathermy device, the deep tissue diathermy device incorporates in addition at least one electrical output device adapted to generate electrical current; and at least two electrodes electrically coupled to said electrical output device and placed on said skin region, wherein all of said electrodes are adapted to simultaneously apply said electrical current to said skin.

In the most preferred embodiments in which the device incorporates a deep tissue diathermy device, it is chosen from the group consisting of ultrasonic diathermy devices, optical diathermy devices, electromagnetic induction diathermy devices, devices for producing sound waves, acoustic, ultrasonic diathermy devices, and devices for direct application of heat. In preferred embodiments in which the deep tissue diathermy device is an optical device, it is adapted to emit light in wavelengths absorbed by subcutaneous tissue such that said subcutaneous tissue is heated. In other preferred embodiments in which the deep tissue diathermy device is a sonic or ultrasonic deep tissue diathermy device, it comprises a device for producing sound waves adapted to emit sound waves of a frequency absorbed by the subcutaneous tissue such that said subcutaneous tissue is heated. All of these means for performing deep tissue diathermy are well-known in the art, and any suitable means for adapting or accommodating them to the present invention may be used.

In yet other preferred embodiments of the invention, control means 140 further comprise processing means adapted to store in a communicable database predetermined parameters defining safe and unsafe treatment parameters, said parameters chosen from the group consisting of time t of said treatment, the temperature of said skin, frequency, power, energy applied by said RF generating means, depth to which said device operates, magnetic field intensity, tissue impedance, specific absorption rate, superficial muscle contractions and any combination thereof; sensing means adapted to sense electromagnetic radiation and heat radiation parameters chosen from a group consisting of time of said treatment, temperature of said tissue frequency, power, intensity of ultrasound irradiation, energy applied by said RF generating means, depth to which said device operates, magnetic field intensity, tissue impedance, specific absorption rate, superficial muscle contractions and any combination thereof; and regulating means adapted to stop the operation of said device if said parameters are determined to be unsafe. Such measuring, processing, and regulating means are well-known in the art, and one skilled in the art will readily understand how to incorporate them into the present device.

In yet other preferred embodiments of the device, control means 140 further comprise a feedback mechanism, adapted to change the RF signal according to predetermined medical needs, and comprising: sensing means adapted to monitor electrotherapy parameters related to the level of skin rejuvenation and viability; processing means, adapted to determine the degree of esthetic improvement in at least one tissue parameter related to the level of skin rejuvenation and vitality; and regulating means adapted to stop the operation of said device when said degree of esthetic improvement reaches a predetermined value. In more preferred embodiments, the electrotherapy parameters and/or the tissue parameters are chosen from the group consisting of dermal tensile forces, tissue impedance, muscle contraction forces, skin elasticity, and any combination thereof. In other preferred parameters, the sensing means are adapted to sense electrotherapy parameters are chosen from the group consisting of time of said treatment, temperature of said tissue, frequency, power, tissue impedance, superficial muscle contractions and any combination thereof. Means for measuring these parameters and for providing such a feedback mechanism and incorporating it into the device are well-known in the art.

In yet other preferred embodiments of the device in which control means 140 incorporate a feedback mechanism, the said processing means are adapted to store in a communicable database predetermined parameters defining safe and unsafe treatment conditions. As above, "unsafe" treatment conditions include those in which tissue damage or discomfort to the person being treated is likely to result. In other preferred parameters, the predetermined parameters are chosen from the group consisting of time of said treatment, temperature of said tissue, frequency, power, tissue impedance, superficial muscle contractions, and any combination thereof.

In yet other embodiments of the invention disclosed herein, it additionally comprises means for massaging said skin.

In yet other embodiments of the invention disclosed herein, at least one of said RF electrodes additionally comprises a hypodermic syringe for penetrating into subcutaneous tissue. By means of such a syringe, a substance with appropriate activity may be injected into the skin during treatment. Non-limiting examples of such substances include a dye to absorb light in embodiments that use optical means for effecting deep tissue diathermy, a muscle relaxant, a local anesthetic, etc.

It is also within the scope of the invention to disclose a method for providing cosmetic improvement to the skin, comprising (a) generating N independent RF signals of predetermined waveforms, frequencies, amplitudes, and relative phases; (b) transmitting each of said N independent RF signals to a pair of electrodes; (c) placing said electrodes in physical contact with said skin; and (d) transmitting energy carried by said RF signals to said skin. It is within the essence of the invention wherein said N independent RF signals are phase-shifted relative to one another. In preferred embodiments, the method is performed by using a device according to any of the embodiments described in detail above.

It is also within the scope of the invention wherein said step of generating N independent RF signals further comprises generating N independent RF signals such that the time-dependent amplitude $A_{t,m}$ of the mth of said N independent RF signals is given by the relationship $A_{t,m}=A_{0,m} \cdot F_m(\omega_m t+\phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth RF signal. While in preferred embodiments of the method, the step of generating N independent RF signals comprises a step in which $A_{0,m}$, $F_m$, and $\omega_m$ are substantially the same for all N signals, and $\phi_m$ is substantially the same for any two pairs of signals m and m+1, this restriction is by no means required, and it is within the scope of the invention to disclose a method in which any or all of them are not identical for all N signals. In preferred embodiments of the method in which $\phi_m$ is substantially the same for all pairs of signals m and m+1, the method further includes a step of providing said phase shift $\phi_m$ for each of said N independent RF signals according to the relationship $\phi_m=\pi k(j-1)/N$, where $0 \le k \le 1$, m=1, 2, 3 . . . N and j=1, 2, 3 . . . ; where N is the number of said pair of electrodes. For example, for one electrode k=1, N=4 and the phase is 135 degrees and for another electrode the phase will be 45 degrees, and another numbers can be combined.

In preferred embodiments of the method, it further includes a step of choosing $F_m$ from the group consisting of sine, cosine, tan, cotangents (cot), sawtooth wave, triangular wave, square wave, rectangular wave, trapezoidal wave, and any combination of the above.

In other preferred embodiments of the method, the step of generating N independent RF signals of predetermined waveforms, frequencies, amplitudes, and relative phases comprises a step of generating N independent RF signals with frequencies between about 1 Hz and about 100 MHz.

In other embodiments of the method, it further comprises a step of transmitting said RF signals in pulses. In preferred embodiments of the method in which the RF signals are transmitted in pulses, the step of transmitting said RF signals in pulses further comprises transmitting said pulses with pulse lengths of between about 0.01 micro-sec and about 1 ms.

According to another embodiment, PEMF are provided. According to another embodiment, the length of said PEMF is between about 0.1 and about 1000 ms.

In other preferred embodiments of the method, it further comprises a step of measuring the temperature of the surface of the skin undergoing cosmetic treatment. In more preferred embodiments of the method in which it further comprises a step of measuring the temperature of the surface of the skin undergoing cosmetic treatment, the step of measuring the temperature of the surface of said skin further comprises measuring the temperature of the surface of said skin by means of at least one sensor chosen from the group consisting of impedance meter adapted to measure impedance across at least one of said pairs of RF electrodes; thermal sensor; thermometer; and any combination thereof.

In other preferred embodiments of the method, it further comprises a step of regulating the amount of RF energy transmitted to the skin undergoing cosmetic treatment such that the temperature of said skin remains within a predetermined range. In more preferred embodiments of the method in which the amount of RF energy transmitted is regulated, the step of regulating the amount of RF energy transmitted to said skin further comprises regulating the amount of RF energy transmitted to said skin such that the temperature of said skin remains in a range of (a) between ambient temperature and 42° C. or (b) between 30° C. and 100° C.

In the most preferred embodiments of the method, it further comprises a step of disposing said electrodes within an electrically insulating casing. This step may include disposing about the distal end of said casing in a geometry chosen from the group consisting of linear; zigzag; on the perimeter of a shape chosen from substantially polygonal, circular, oval, or irregular; within the area of a shape chosen from substantially polygonal, circular, oval, or irregular; and any combination of the above.

In other preferred embodiments of the method, it further comprises a step of transmitting to said skin a power of between 1 W and 700 W by said RF electrodes and said RF generating means.

In other preferred embodiments of the method, it further comprises a step of providing a cosmetic improvement to the skin chosen from the group consisting of skin rejuvenation, reduction of the number of wrinkles, reduction of the depth of wrinkles, reduction of cellulite, skin tightening, circumferential reduction, and any combination of the above.

In other preferred embodiments of the method, it further comprises a step of cooling the skin undergoing cosmetic treatment. In the most preferred embodiments of the method in which it comprises a step of cooling the skin undergoing cosmetic treatment, the step of cooling said skin further comprises cooling said skin by the use means chosen from the group consisting of a Peltier effect cooling device, irrigation with cool water, and means for blowing air across the skin.

In other preferred embodiments of the method, it further comprises a step of heating said skin by means of said RF electrodes.

In other preferred embodiments of the method, it further comprises a step of performing deep tissue diathermy. In more preferred embodiments of the invention in which it comprises a step of performing deep tissue diathermy, the of performing deep tissue diathermy further comprises performing deep tissue diathermy by a method chosen from the group consisting of emitting RF radiation and producing electrical current absorbed by subcutaneous tissue.

In the most preferred embodiments of the method in which it includes a step of performing deep tissue diathermy, the step of performing deep tissue diathermy further comprises generating RF electromagnetic energy by use of at least one electrical output device; coupling at least two electrodes to said at least one electrical output device; and applying simultaneously said RF energy to said skin. Additionally or alternatively, the step of performing deep tissue diathermy may further comprise generating electrical current by means of at least one electrical output; coupling electrically at least two electrodes electrically to said electrical output; placing said electrodes on said skin; and applying simultaneously said electrical current to said skin.

In other preferred embodiments of the method that include a step of performing deep tissue diathermy, the step of performing deep tissue diathermy further comprises performing deep tissue diathermy by a means chosen from the group consisting of ultrasonic diathermy devices, optical diathermy devices, electromagnetic induction diathermy devices, devices for producing sound waves, ultrasonic diathermy devices, and devices for direct application of heat.

In other preferred embodiments of the method that include a step of performing deep tissue diathermy, the step of performing deep tissue diathermy further comprises performing deep tissue diathermy by means of an optical device adapted to emit light in wavelengths absorbed by subcutaneous tissue such that said subcutaneous tissue is heated.

In other preferred embodiments of the method that include a step of performing deep tissue diathermy, the step of performing deep tissue diathermy further comprises performing deep tissue diathermy by means of a device for producing sound waves adapted to emit sound waves of a frequency absorbed by the subcutaneous tissue such that said subcutaneous tissue is heated.

In other preferred embodiments of the method that include a step of performing deep tissue diathermy, the method further comprises steps of monitoring physical tissue parameters; and changing at least one of (a) the amount of heat applied and (b) the form of said RF in response to the values of said physical tissue parameters.

In yet other preferred embodiments of the method that include a step of performing deep tissue diathermy, it further comprises steps of storing in a communicable database predetermined parameters defining safe and unsafe treatment parameters, said parameters chosen from the group consisting of time t of said treatment, the temperature of said skin, frequency, power, energy applied by said RF generating means, depth to which said device operates, magnetic field intensity, tissue impedance, specific absorption rate, superficial muscle contractions and any combination thereof; sensing electromagnetic radiation and heat radiation parameters chosen from a group consisting of time of said treatment, temperature of said tissue, frequency, power, intensity of ultrasound irradiation, energy applied by said RF generating means, depth to which said device operates, magnetic field intensity, tissue impedance, specific absorption rate, superficial muscle contractions and any combination thereof; and ceasing the continued performance of said method if said parameters are determined to be unsafe.

In yet other preferred embodiments of the method that include a step of performing deep tissue diathermy, it further comprises steps of monitoring electrotherapy parameters related to the level of skin rejuvenation and viability; determining the degree of esthetic improvement in at least one tissue parameter related to the level of skin rejuvenation and vitality; and ceasing the continued performance of said method when said degree of esthetic improvement reaches a predetermined value. In more preferred embodiments, the step of monitoring electrotherapy parameters further comprises monitoring at least one parameter chosen from the group consisting of dermal tensile forces, tissue impedance, muscle contraction forces, and skin elasticity. Alternatively or additionally, the step of determining the degree of esthetic improvement in at least one tissue parameter related to the level of skin rejuvenation and vitality further comprises a of determining the degree of esthetic improvement in at least one parameter chosen from the group consisting of dermal tensile forces, tissue impedance, muscle contraction forces, and skin elasticity; it may further include a step of monitoring electrotherapy parameters chosen from the group consisting of time of said treatment, temperature of said tissue, frequency, power, tissue impedance, superficial muscle contractions and any combination thereof. In yet other preferred embodiments of the method that include a step of performing deep tissue diathermy, it further comprises a step of storing in a communicable database predetermined parameters defining safe and unsafe treatment conditions. In more preferred embodiments, the step of storing in a communicable database predetermined parameters defining safe and unsafe treatment conditions further comprises storing in a communicable database at least one parameters chosen from the group consisting of time of said treatment, temperature of said tissue, frequency, power, tissue impedance, and superficial muscle contractions.

In yet other preferred embodiments of the method, it further comprises a step of massaging the skin undergoing cosmetic treatment.

In yet other preferred embodiments of the method, it further comprises a step of incorporating a hypodermic syringe for penetrating into subcutaneous tissue into at least one of said electrodes.

It should be emphasized that the above mentioned application of RF energy is given as an example and the same method can be applied by using any type of energy source (e.g., ultrasound, light, laser, electrical energy, magnetic field and any combination thereof).

Therefore, it is a core concept of the present invention to provide a device for improving the cosmetic appearance of the skin, comprising:

N pairs of electrodes, each of said pairs in independent communication with energy generating means, said electrodes configured to transmit said energy to said skin;

energy generating means for generating N independent energy signals of predetermined waveforms, frequencies, amplitudes, and relative phases;

control means for controlling the output of said energy generating means, said control means in communication with said energy generating means; and, an electrically insulating casing adapted to hold said electrodes such that said electrodes may be placed in simultaneous physical contact with said skin;

wherein said N independent energy signals are phase shifted relative to one another.

According to another embodiment of the present invention, the time-dependent amplitude $A_{t,m}$ of the mth of said N independent energy signals is given by the relationship $A_{t,m}=A_{0,m}\cdot F_m(\omega_m t+\phi_m)$, where $A_{0,m}$ is a predetermined constant which greater than or equals to 1, $F_m$ is a predetermined periodic function of time, $\omega_m$ is the angular frequency of the mth RF signal, and $\phi_m$ is a predetermined phase shift of the mth energy signal.

According to another embodiment of the present invention, for each of said N independent energy signals, $\phi_m=\pi k(j-1)/N$, where $0\leq k\leq 1$, m=1, 2, 3 ... N and j=1, 2, 3 ... ; where N is the amount of said electrodes pairs.

According to another embodiment of the present invention, the energy is selected from a group consisting of ultrasound, laser, light, electrical energy, magnetic field and any combination thereof.

According to another embodiment of the present invention, $F_m$ is chosen from the group consisting of sine, cosine, tan, cotangents (cot), sawtooth wave, triangular wave, square wave, rectangular wave, trapezoidal wave, and any combination of the above.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims, with the proper scope determined only by the broadest interpretation of the claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A device for improving the cosmetic appearance of the skin, comprising:
   a. an energy generator configured to generate N independent RF signals of predetermined waveforms, frequencies, amplitudes, and relative phases;
   b. N pairs of RF electrodes, each of said N pairs of RF electrodes in independent communication with said RF generators, each of said N pairs of RF electrodes configured to transmit RF energy to said skin; a controller configured to control the output of said RF generators, said controller in communication with said RF generator; and,
   c. an electrically insulating casing configured to hold said N pairs of RF electrodes such that said N pairs of RF electrodes may be placed in simultaneous physical contact with said skin;
   wherein said N independent RF signals are phase shifted relative to one another;
   further wherein the time-dependent amplitude $A_{t,m}$ of the mth of said N independent RF signals is given by the relationship $A_{t,m}=A_{0,m}\cdot F_m(\omega_m t+\phi_m)$, where $A_{0,m}$ is a predetermined constant which is greater than or equal to 1, $F_m$ is a predetermined periodic function of time, $\omega_m$ is the angular frequency of the mth RF signal, and $\phi_m$ is a predetermined phase shift of the mth RF signal; for each of said N independent RF signals, $\phi_m=\pi k(j-1)/N$, where $0\leq k\leq 1$, m=1, 2, 3 ... N and j is an integer equal to or greater than 1; where N is the number of said RF electrode pairs; $F_m$ is chosen from a group consisting of sine, cosine, tan, cotangents (cot), sawtooth wave, triangular wave, square wave, rectangular wave, trapezoidal wave, and any combination of the above.

2. The device according to claim 1, wherein at least one of the following is being held true:
   a. each of said predetermined frequencies is between about 1 Hz and about 100 MHz;
   b. said RF signals are transmitted in either a continues mode or in pulses; when the RF is applied in pulses, the length of said pulses is between about 0.01 micro-sec and about 1 ms; length of said pulses is between about 0.1 and about 1000 ms;
   c. additionally comprising a mechanism configured to apply Pulsed Electromagnetic Field Therapy (PEMF);
   d. further comprising at least one temperature sensor configured to measure the temperature of the surface of said skin; said at least one sensor chosen from a group consisting of impedance meter configured to measure impedance across at least one of said N pairs of RF electrodes; thermal sensor; thermometer; and any combination thereof; said at least one temperature sensor is configured to either come into contact with the skin or not be in contact with the skin; said controller is programmed to regulate the amount of RF energy transmitted to said skin such that the temperature of said skin remains within a predetermined range; said predetermined range is between ambient temperature and 42° C.;

e. said N pairs of RF electrodes are disposed about a distal end of said casing in a geometry chosen from a group consisting of linear; zigzag; on the perimeter of a shape chosen from substantially polygonal, circular, oval, or irregular; within the area of a shape chosen from polygonal, circular, oval, or irregular; and any combination of the above;

f. power transmitted by said RF electrodes and said RF generators to said skin is between 1 W and 700 W;

g. said cosmetic improvement is chosen from a group consisting of skin rejuvenation, reduction of the number of wrinkles, reduction of the depth of wrinkles, reduction of cellulite, skin tightening, circumferential reduction, and any combination of the above;

h. further comprising a cooling mechanism configured to cool said skin;

i. said cooling mechanism is chosen from a group consisting of a Peltier effect cooling device, irrigation with cool water, and a mechanism for blowing air across the skin;

j. said N pairs of RF electrodes are further configured to provide heat to said skin;

k. additionally comprising a skin massaging section; and, l. at least one of said N pairs of RF electrodes comprises a hypodermic syringe for penetrating into subcutaneous tissue.

3. The device according to claim 1, further comprising a deep tissue diathermy device.

4. The device according to claim 3, wherein at least one of the following is being held true:

a. said deep tissue diathermy device is chosen from a group consisting of: a device emitting RF radiation and any other means configured for producing electrical current absorbed by subcutaneous tissue;

b. said deep tissue diathermy device further comprises at least one electrical output device configured to generate RF electromagnetic energy; and, at least two electrodes electrically coupled to said electrical output device and placed on said skin region, wherein all said electrodes are configured to simultaneously apply said RF electromagnetic energy to said skin;

c. said deep tissue diathermy device further comprises at least one electrical output device configured to generate electrical current; and, at least two electrodes electrically coupled to said electrical output device and placed on said skin region, wherein all of said electrodes are configured to simultaneously apply said electrical current to said skin;

d. said deep tissue diathermy device is chosen from a group consisting of acoustic diathermy devices, optical diathermy devices, electromagnetic induction diathermy devices, devices for producing sound waves, ultrasonic diathermy devices, and devices for direct application of heat;

e. said deep tissue diathermy device is an optical device configured to emit light in wavelengths absorbed by subcutaneous tissue such that said subcutaneous tissue is heated;

f. said deep tissue diathermy device is a device for producing sound waves configured to emit sound waves of a frequency absorbed by the subcutaneous tissue such that said subcutaneous tissue is heated;

g. said controller is configured to monitor physical tissue parameters and changes at least one of (a) the amount of heat applied and (b) the form of said RF in response to the values of said physical tissue parameters; and, h. said controller further comprises:
    a processor that is configured to direct the storage, in a communicable database, predetermined parameters defining safe and unsafe treatment parameters, said parameters chosen from a group consisting of time of said treatment, the temperature of said skin, frequency, power, energy applied by said RF generator, depth to which said device operates, magnetic field intensity, tissue impedance, specific absorption rate, superficial muscle contractions and any combination thereof;
    a sensor that is configured to senses electromagnetic radiation and heat radiation parameters chosen from a group consisting of time of said treatment, temperature of said tissue, frequency, power, intensity of ultrasound irradiation, energy applied by said RF generator, depth to which said device operates, magnetic field intensity, tissue impedance, specific absorption rate, superficial muscle contractions and any combination thereof; and,
    a regulator that is configured to stop the operation of said device if said parameters are determined to be unsafe.

5. The device according to claim 1, wherein said controller is configured to change said N independent RF signals according to predetermined medical needs, and comprising:

a. at least one sensor that is configured to monitor electrotherapy parameters related to the level of skin rejuvenation and viability;

b. a processor that is configured to determines the degree of esthetic improvement in at least one tissue parameter related to the level of skin rejuvenation and vitality; and, c. a regulator that is configured to stop the operation of said device when said degree of esthetic improvement reaches a predetermined value.

6. The device according to claim 5, wherein at least one of the following is being held true:

a. said electrotherapy parameters are chosen from a group consisting of dermal tensile forces, tissue impedance, muscle contraction forces, skin elasticity, and any combination thereof;

b. said at least one tissue parameter is chosen from a group consisting of dermal tensile forces, tissue impedance, muscle contraction forces, skin elasticity, and any combination thereof;

c. wherein said at least one sensor that is configured to monitors electrotherapy parameters is chosen from a group consisting of time of said treatment, temperature of said tissue, frequency, power, tissue impedance, superficial muscle contractions and any combination thereof; and, d. said processor is configured to direct storage, in a communicable database, predetermined parameters defining safe and unsafe treatment conditions; said predetermined parameters are chosen from a group consisting of time of said safe and unsafe treatment, temperature of said tissue, frequency, power, tissue impedance, superficial muscle contractions, and any combination thereof.

7. A device for improving the cosmetic appearance of the skin, comprising:

a. an energy generator configured to generate N independent energy signals selected from a group consisting of acoustic energy, ultrasound, light, laser, electrical energy, magnetic field and any combination thereof; each of said N independent energy signals is characterized by a predetermined waveform, frequency, amplitude, and relative phase;

b. N pairs of electrodes, each of said N pairs of RF electrodes in independent communication with said energy generator, said N pairs of electrodes configured to transmit said energy to said skin;

c. a controller that is configured to control the output of said energy generator, said controller in communication with said energy generator; and, d. an electrically insulating casing configured to hold said electrodes such that said electrodes may be placed in simultaneous physical contact with said skin;

wherein said N independent energy signals are phase shifted relative to one another;

further wherein the time-dependent amplitude $A_{t,m}$ of the mth of said N independent energy signals is given by the relationship $A_{t,m}=A_{0,m} \cdot F_m(\omega_m t+\phi_m)$, where $A_{0,m}$ is a predetermined constant which is greater than or equal to 1, $F_m$ is a predetermined periodic function of time, $\omega_m$ is the angular frequency of the mth RF signal, and $\phi_m$ is a predetermined phase shift of the mth energy signal; for each of said N independent energy signals, $\phi_m=\pi k(j-1)/N$, where $0 \leq k \leq 1$, m=1, 2, 3 . . . N and j is an integer equal to or greater than 1; where N is the number of said electrode pairs; said predetermined periodic function of time $F_m$ is chosen from a group consisting of sine, cosine, tan, cotangents (cot), sawtooth wave, triangular wave, square wave, rectangular wave, trapezoidal wave, and any combination of the above.

8. The device according to claim 7, wherein at least one of the following is being held true:
a. said energy is selected from a group consisting of ultrasound, light, laser, electrical energy, magnetic field and any combination thereof;
b. said N independent energy signals are transmitted in either a continues mode or in pulses; when said energy is applied in pulses, the length of said pulses is between about 0.01 micro-sec and about 1 ms;
c. additionally comprising a mechanism configured to apply Pulsed Electromagnetic Field Therapy (PEMF); the length of said pulses is between about 0.1 and about 1000 ms;
d. said N pairs of RF electrodes are disposed about a distal end of said casing in a geometry chosen from a group consisting of linear; zigzag; on the perimeter of a shape chosen from substantially polygonal, circular, oval, or irregular; within the area of a shape chosen from substantially polygonal, circular, oval, or irregular; and any combination of the above;
e. power transmitted by said N pairs of RF electrodes and said energy generator to said skin is between 1 W and 700 W;
f. said cosmetic improvement is chosen from a group consisting of skin rejuvenation, reduction of the number of wrinkles, reduction of the depth of wrinkles, reduction of cellulite, skin tightening, circumferential reduction, and any combination of the above;
g. further comprising a cooling mechanism configured to cool said skin; said cooling mechanism is chosen from a group consisting of a Peltier effect cooling device, irrigation with cool water, and a mechanism for blowing air across the skin;
h. said energy is configured to provide heat to said skin; and,
i. additionally comprising a mechanism for massaging said skin.

9. The device according to claim 7, further comprising at least one temperature sensor configured to measure the temperature of the surface of said skin, wherein at least one of the following is being held true:
a. said at least one temperature sensor selected from a group consisting of: impedance meter configured to measure impedance across at least one of said N pairs of RF electrodes; thermal sensor; thermometer; and any combination thereof;
b. said at least one temperature sensor either comes into contact with the skin or is not in contact with the skin; and,
c. said controller programmed to regulate the amount of energy transmitted to said skin such that the temperature of said skin remains within a predetermined range; said predetermined range is between ambient temperature and 42° C.

10. The device according to claim 7, further comprising a deep tissue diathermy device; wherein at least one of the following is being held true:
a. said deep tissue diathermy device is chosen from a group consisting of any devices emitting RF radiation and any other means configured for producing electrical current absorbed by subcutaneous tissue;
b. said deep tissue diathermy device further comprises: at least one electrical output device configured to generate RF electromagnetic energy; and, at least two electrodes electrically coupled to said electrical output device and placed on said skin region, wherein all said electrodes are configured to simultaneously apply said RF energy to said skin;
c. said deep tissue diathermy device further comprises: at least one electrical output device configured to generate electrical current; and, at least two electrodes electrically coupled to said electrical output device and placed on said skin region, wherein all of said electrodes are configured to simultaneously apply said electrical current to said skin;
d. said deep tissue diathermy device is chosen from a group consisting of acoustic (e.g., ultrasonic) diathermy devices, optical diathermy devices, electromagnetic induction diathermy devices, devices for producing sound waves, ultrasonic diathermy devices, and devices for direct application of heat;
e. said deep tissue diathermy device is an optical device configured to emit light in wavelengths absorbed by subcutaneous tissue such that said subcutaneous tissue is heated; and,
f. said deep tissue diathermy device is a device for producing sound waves configured to emit sound waves of a frequency absorbed by the subcutaneous tissue such that said subcutaneous tissue is heated.

11. The device according to claim 7, wherein said controller is configured to change said energy signal according to predetermined medical needs, and comprising:
a. At least one sensor that is configured to monitor electrotherapy parameters related to the level of skin rejuvenation and viability;
b. a processor that is configured to determines the degree of esthetic improvement in at least one tissue parameter related to the level of skin rejuvenation and vitality; and,
c. a regulator that is configured to stop the operation of said device when said degree of esthetic improvement reaches a predetermined value.

12. The device according to claim 11, wherein at least one of the following is being held true:

a. said electrotherapy parameters are chosen from a group consisting of dermal tensile forces, tissue impedance, muscle contraction forces, skin elasticity, and any combination thereof;
b. said at least one tissue parameter is chosen from a group consisting of dermal tensile forces, tissue impedance, muscle contraction forces, skin elasticity, and any combination thereof;
c. said at least one sensor that is configured to monitors electrotherapy parameters is chosen from a group consisting of time of said treatment, temperature of said tissue, frequency, power, tissue impedance, superficial muscle contractions and any combination thereof;
d. said processor is configured to store in a communicable database predetermined parameters defining safe and unsafe treatment conditions; and
e. said predetermined parameters are chosen from a group consisting of time of said treatment, temperature of said tissue, frequency, power, tissue impedance, superficial muscle contractions, and any combination thereof.

13. A device for improving the cosmetic appearance of the skin, comprising:
   a. N pairs of electrodes, each of said N pairs of electrodes characterized by a proximal end and a distal end, each of said pairs of electrodes in independent communication with said energy generator, said N pairs of electrodes configured to transmit said energy to said skin;
   b. an energy generator that generates N independent energy signals selected from a group consisting of acoustic energy, ultrasound, light, laser, electrical energy, magnetic field and any combination thereof; each of said N independent energy signals is characterized by predetermined waveforms, frequencies, amplitudes, and relative phases;
   c. a controller configured to control the output of said energy generator, said controller in communication with said energy generator; and,
   d. an electrically insulating casing configured to hold said electrodes at said proximal end such that said electrodes may be placed in simultaneous physical contact with said skin;
wherein said N independent energy signals are phase shifted relative to one another;
further wherein the time-dependent amplitude $A_{t,m}$ of the mth of said N independent energy signals is given by the relationship $A_{t,m}=A_{0,m} \cdot F_m(\omega_m t+\phi_m)$, where $A_{0,m}$ is a predetermined constant which is greater than or equal to 1, $F_m$ is a predetermined periodic function of time, $\omega_n$ is the angular frequency of the mth RF signal, and $\phi_m$ is a predetermined phase shift of the mth energy signal; for each of said N independent energy signals, $\phi_m=\pi k(j-1)/N$, where $0 \leq k \leq 1$, m=1, 2, 3 . . . N and j is an integer equal to or greater than 1; where N is the amount of said electrode pairs.

14. The device according to claim 13, wherein at least one of the following is being held true:
   a. said energy is selected from a group consisting of ultrasound, light, laser, electrical energy, magnetic field and any combination thereof;
   b. said predetermined periodic function of time $F_m$ is chosen from a group consisting of sine, cosine, tan, cotangents (cot), sawtooth wave, triangular wave, square wave, rectangular wave, trapezoidal wave, and any combination of the above;
   c. said N independent energy signals are transmitted in either a continues mode or in pulses; when said energy is applied in pulses, the length of said pulses is between about 0.01 micro-sec and about 1 ms;
   d. additionally comprising a mechanism configured to apply Pulsed Electromagnetic Field Therapy (PEMF); the length of said pulses is between about 0.1 and about 1000 ms;
   e. said N pairs of RF electrodes are disposed about a distal end of said casing in a geometry chosen from a group consisting of linear; zigzag; on the perimeter of a shape chosen from substantially polygonal, circular, oval, or irregular; within the area of a shape chosen from substantially polygonal, circular, oval, or irregular; and any combination of the above;
   f. power transmitted by said N pairs of RF electrodes and said energy generator to said skin is between 1 W and 700 W;
   g. said cosmetic improvement is chosen from a group consisting of skin rejuvenation, reduction of the number of wrinkles, reduction of the depth of wrinkles, reduction of cellulite, skin tightening, circumferential reduction, and any combination of the above;
   h. further comprising a cooling mechanism configured to cool said skin; said cooling mechanism is chosen from a group consisting of: a Peltier effect cooling device, irrigation with cool water, and a mechanism for blowing air across the skin;
   i. said energy is configured to provide heat to said skin; and,
   j. additionally comprising a mechanism for massaging said skin.

15. The device according to claim 13, further comprising at least one temperature sensor configured to measure the temperature of the surface of said skin, wherein at least one of the following is being held true:
   a. said at least one temperature sensor is selected from a group consisting of impedance meter configured to measure impedance across at least one of said N pairs of RF electrodes; thermal sensor; thermometer; and any combination thereof;
   b. said at least one temperature sensor either comes into contact with the skin or is not in contact with the skin; and,
   c. said controller programmed to regulate the amount of energy transmitted to said skin such that the temperature of said skin remains within a predetermined range; said predetermined range is between ambient temperature and 42° C.

16. The device according to claim 13, further comprising a deep tissue diathermy device; wherein at least one of the following is being held true:
   a. said deep tissue diathermy device is chosen from a group consisting of a device emitting RF radiation and any other means configured for producing electrical current absorbed by subcutaneous tissue;
   b. said deep tissue diathermy device further comprises: at least one electrical output device configured to generate RF electromagnetic energy; and, at least two electrodes electrically coupled to said electrical output device and placed on said skin region, wherein all said electrodes are configured to simultaneously apply said RF energy to said skin;
   c. said deep tissue diathermy device further comprises: at least one electrical output device configured to generate electrical current; and, at least two electrodes electrically coupled to said electrical output device and placed on said skin region, wherein all of said electrodes are configured to simultaneously apply said electrical current to said skin;

d. said deep tissue diathermy device is chosen from a group consisting of acoustic (e.g., ultrasonic) diathermy devices, optical diathermy devices, electromagnetic induction diathermy devices, devices for producing sound waves, ultrasonic diathermy devices, and devices for direct application of heat;

e. said deep tissue diathermy device is an optical device configured to emit light in wavelengths absorbed by subcutaneous tissue such that said subcutaneous tissue is heated; and, f. said deep tissue diathermy device is a device for producing sound waves configured to emit sound waves of a frequency absorbed by the subcutaneous tissue such that said subcutaneous tissue is heated.

17. The device according to claim 13, wherein said controller is configured to change said energy signal according to predetermined medical needs, and comprising:

a. at least one sensor that is configured to monitor electrotherapy parameters related to the level of skin rejuvenation and viability;

b. a processor that is configured to determine the degree of esthetic improvement in at least one tissue parameter related to the level of skin rejuvenation and vitality; and, c. a regulator that is configured to stop the operation of said device when said degree of esthetic improvement reaches a predetermined value.

18. The device according to claim 17, wherein at least one of the following is being held true:

a. said electrotherapy parameters are chosen from a group consisting of dermal tensile forces, tissue impedance, muscle contraction forces, skin elasticity, and any combination thereof;

b. said at least one tissue parameter is chosen from a group consisting of dermal tensile forces, tissue impedance, muscle contraction forces, skin elasticity, and any combination thereof;

c. said at least one sensor that monitors electrotherapy parameters is chosen from a group consisting of time of said treatment, temperature of said tissue, frequency, power, tissue impedance, superficial muscle contractions and any combination thereof;

d. said processor is configured to store in a communicable database predetermined parameters defining safe and unsafe treatment conditions; and e. said predetermined parameters are chosen from a group consisting of time of said treatment, temperature of said tissue, frequency, power, tissue impedance, superficial muscle contractions, and any combination thereof.

* * * * *